United States Patent [19]
Jones et al.

[11] Patent Number: 4,930,058
[45] Date of Patent: May 29, 1990

[54] QUICK-RELEASE DENTAL LIGHT HANDLE

[75] Inventors: Arthur L. Jones; George McGaha, both of Charlotte, N.C.

[73] Assignee: The Pelton & Crane Company, Charlotte, N.C.

[21] Appl. No.: 434,387

[22] Filed: Nov. 9, 1989

[51] Int. Cl.⁵ .............................................. F21L 15/12
[52] U.S. Cl. .................................... 362/400; 362/371; 362/399; 362/804
[58] Field of Search ............... 362/269, 285, 371, 399, 362/400, 419, 804; 16/114 R

[56] References Cited
U.S. PATENT DOCUMENTS

| | | | |
|---|---|---|---|
| D. 201,038 | 5/1965 | Sullivan et al. | D48/20 |
| D. 264,508 | 5/1982 | Williams et al. | D26/61 |
| 3,191,023 | 6/1965 | Sullivan et al. | 240/41.15 |
| 3,887,801 | 6/1975 | Ilzig et al. | 240/1.4 |
| 4,254,454 | 3/1981 | Hardin, Jr. | 362/282 |
| 4,316,237 | 2/1982 | Yamada et al. | 362/33 |
| 4,605,124 | 8/1986 | Sandel et al. | 16/114 R |

Primary Examiner—Stephen F. Husar
Attorney, Agent, or Firm—Lawrence C. Edelman

[57] ABSTRACT

A unitary, quick-release handle for use on dental, medical and similar lighting fixtures has a quick-release feature which permits the handle to be quickly and easily removed and then placed in an autoclave for purposes of sterilization.

18 Claims, 4 Drawing Sheets

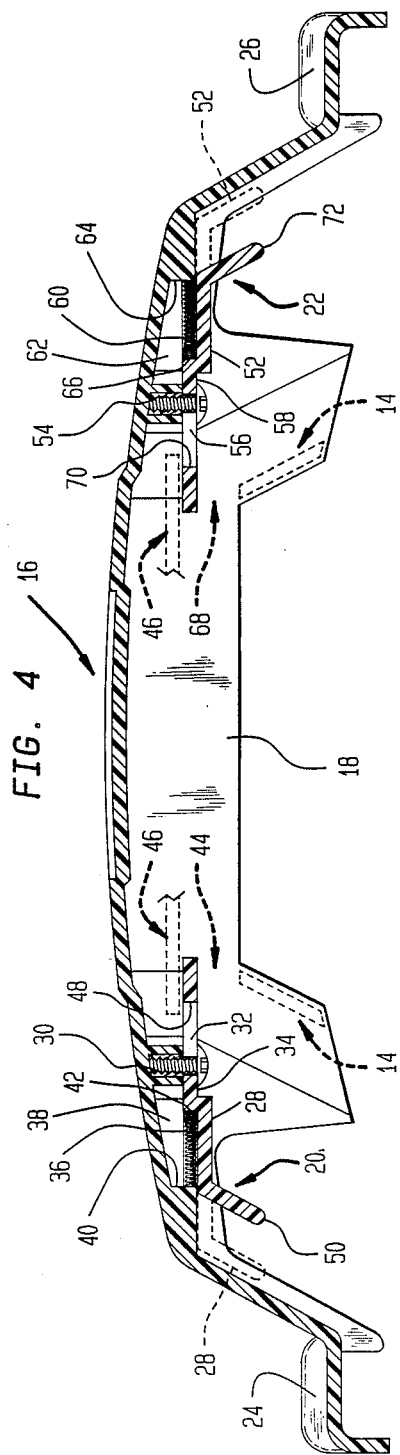

QUICK-RELEASE DENTAL LIGHT HANDLE

FIELD OF THE INVENTION

The present invention relates to handles for use on a dental, medical or other similar lighting fixture, and, more particularly, to such handles which are detachable so that they can be removed, sterilized and reused.

BACKGROUND OF THE INVENTION

In lighting fixtures of the type normally utilized in the dental, medical and other similar fields, handles are commonly employed so that the dentist, doctor or any other person performing the operation or treatment can adjust the position of the fixture. Typically, the dentist, doctor or other person performing the operation or treatment makes such an adjustment manually (i.e., by gripping the handle with his or her hand or hands). The handles, therefore, present a potential health problem because of the possibility that they could serve as a vehicle for transmitting infection and/or disease from one patient to another. Nowadays, the significance of this problem has taken on new dimensions due to the public's increasing concern over the transmission of communicable diseases, such as Acquired Immune Deficiency Syndrome (AIDS).

Over the years, various attempts have been made to insure the sterile or aseptic condition of handles for dental, medical or similar lighting fixtures. For instance, disposable covers and antiseptic sprays have been used. Also, detachable handles have been proposed (see, for instance, U.S. Pat. Nos. 4,254,454 and 4,254,455, both of which are owned by the assignee of the present invention and which disclose lighting fixtures that have been commercially successful for a number of years), some even with the specific object of being removable for the purpose of sterilization (see, for instance, U.S. Pat. Nos. 3,887,801 and 4,316,237). The mechanisms employed by these prior art devices to render them removable are, however, disadvantageous because of their inability to be removed quickly and easily or because of other inadequacies or inefficiencies in their construction and design.

SUMMARY OF THE INVENTION

The present invention overcomes the problems and shortcomings discussed above by providing a unitary, quick-release handle for use on dental, medical and other similar lighting fixtures. More particularly, the new and improved handle includes a pair of handgrips, each handgrip being positioned on a corresponding end of the handle so as to be readily accessible to an operator. A quick-release mechanism is located between the ends of the handle for the purpose of releasably attaching the handle to the lighting fixture. Once removed from the lighting fixture, the handle can be placed in an autoclave for sterilization prior to reuse. While the removed handle is being sterilized, a replacement handle can be attached to the lighting fixture so that the fixture may remain in operation during the sterilization of the removed handle.

In one embodiment, the quick-release mechanism includes a pair of spring-loaded latches which are mounted for sliding movement within the handle between a latched position and an unlatched position. Each of the latching mechanisms is trigger-actuated so that it can be engaged by a finger of an operator, who can then manually move it from its latched position to its unlatched position. Each of the latching mechanisms is also spring-loaded so that it can be automatically returned from its unlatched position to its latched position.

BRIEF DESCRIPTION OF THE DRAWINGS

For a better understanding of the present invention, reference is made to the following detailed description of an exemplary embodiment considered in conjunction with the accompanying drawings, in which:

FIG. 4 is a cross-sectional view, taken along section line IV—IV in FIG. 3 and looking in the direction of the arrows, of the handle illustrated in FIG. 3, portions of the lighting fixture housing being shown in phantom to facilitate consideration and discussion.

DETAILED DESCRIPTION OF THE EXEMPLARY EMBODIMENT

Although the present invention is applicable to many different types of lighting fixtures, it is especially suitable for use on dental lighting fixtures and the like. Accordingly, the present invention will be described in connection with a dental lighting fixture.

Figure 1:
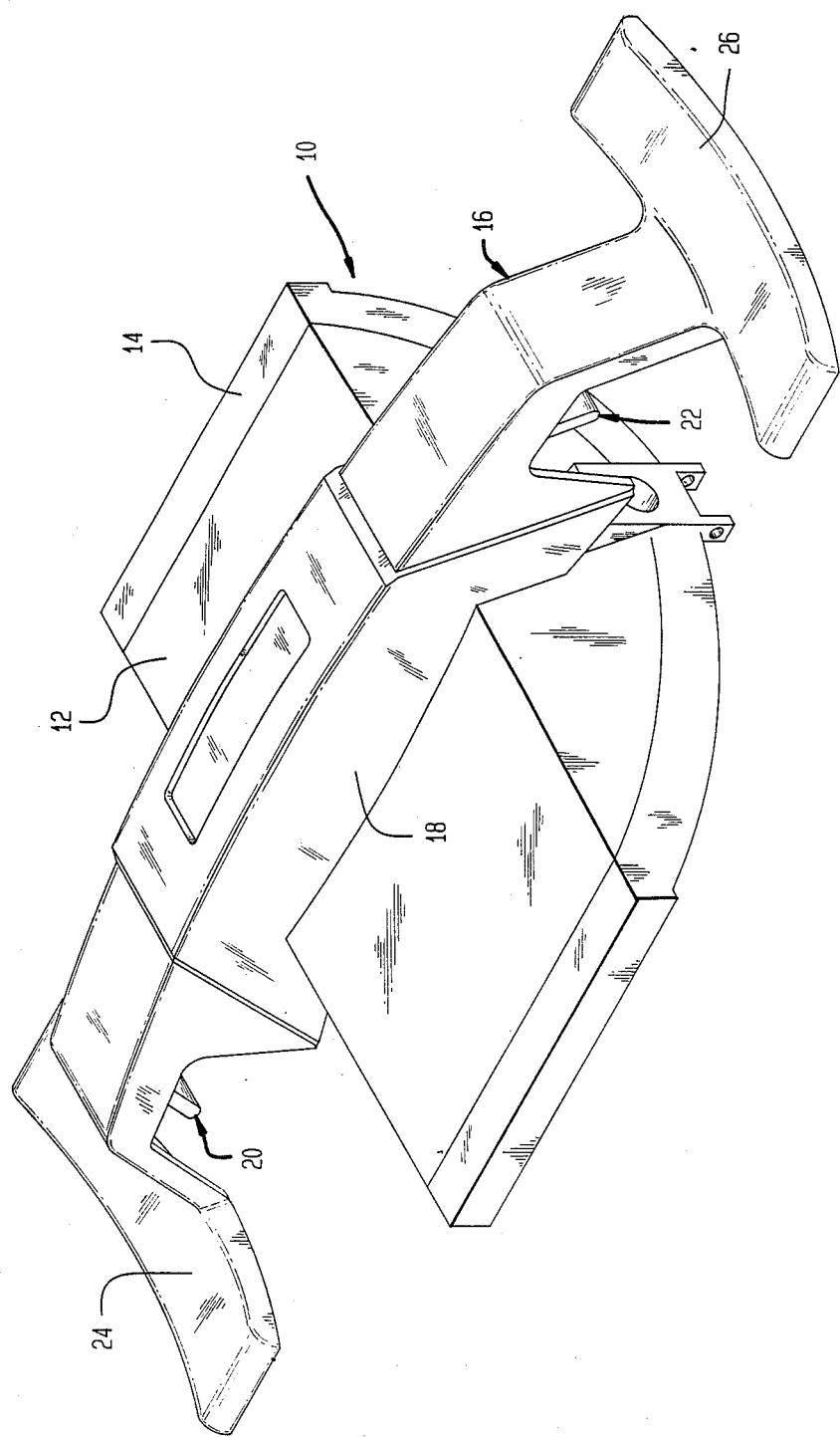
FIG. 1 is a perspective view of a dental light housing equipped with a handle constructed in accordance with one exemplary embodiment of the present invention.

With reference to FIG. 1, a dental lighting fixture has a housing 10 for a light bulb (not shown) which is at least partially protected by a shield 12 and a frame 14. A handle 16, which includes a body 18 bridging the shield 14 so as to provide additional protection for the light bulb, is releaseably attached to the frame 14 of the housing 10 by a pair of latching mechanisms 20, 22. Handgrips 24, 26 extend outwardly from opposite ends of the body 18 so that the handle 16 can be gripped by the dentist or his or her assistant for the purpose of adjusting the position of the lighting fixture.

Figure 2:
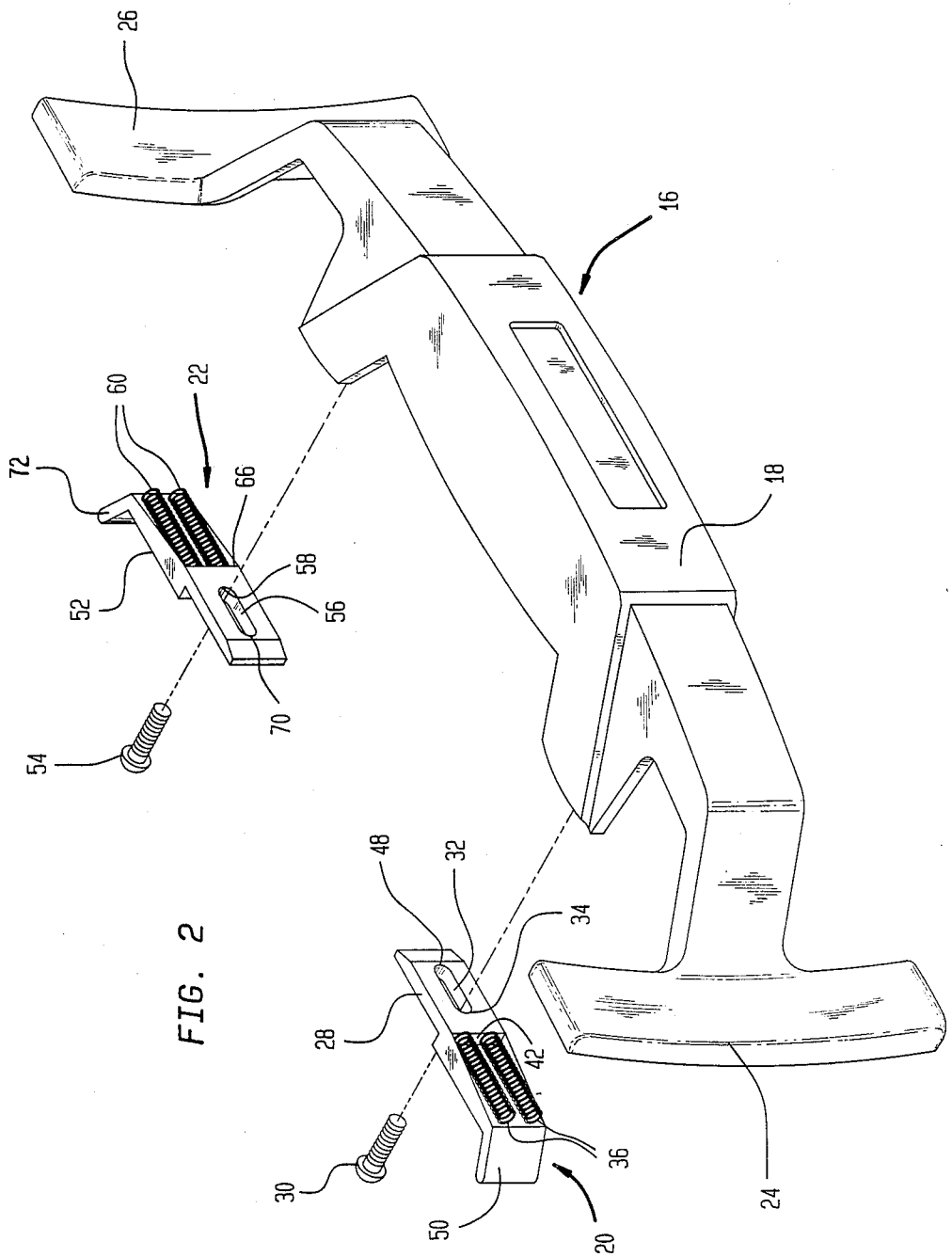
FIG. 2 is an exploded perspective view of the handle illustrated in FIG. 1.
Figure 3:
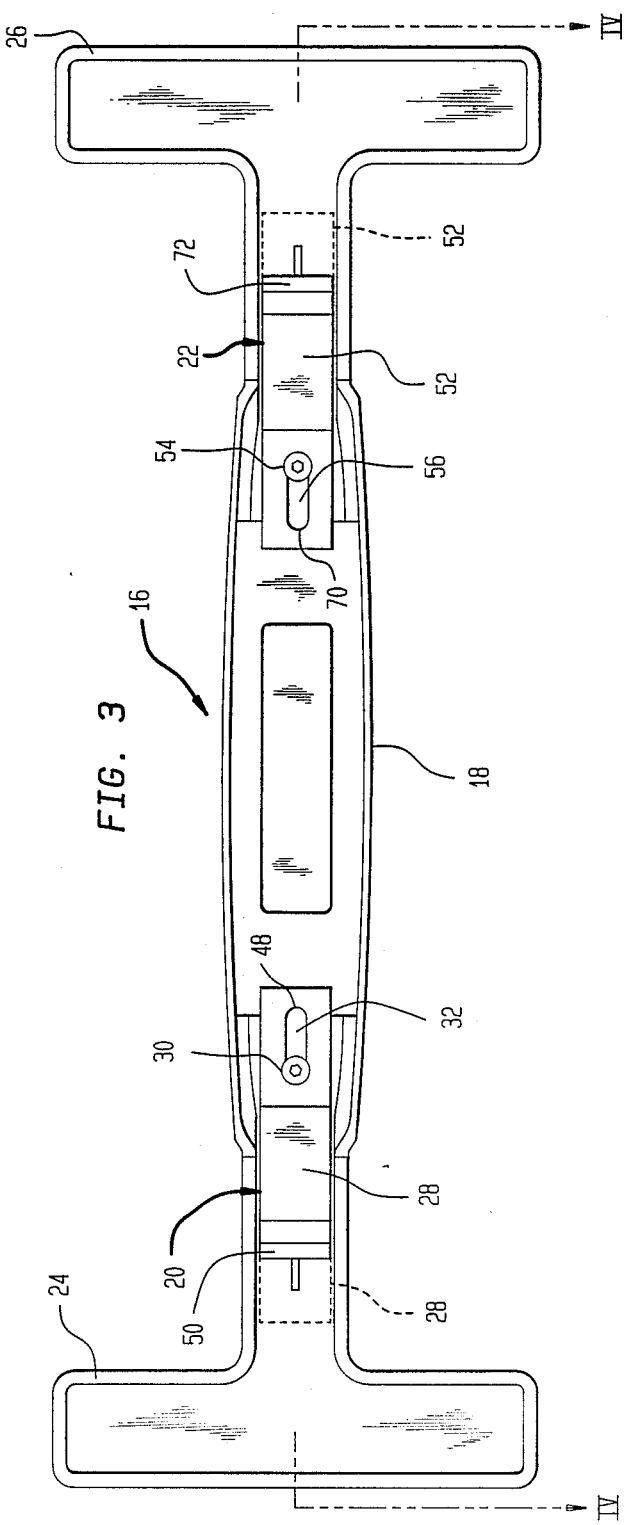
FIG. 3 is a rear elevational view of the handle illustrated in FIG. 1.

Referring now to FIGS. 2-4, the latching mechanism 20 includes a slide 28 which is slideably received within the body 18 adjacent to the handgrip 24 such that the slide 28 can be moved between a latched position (indicated by solid lines in FIGS. 3 and 4) and an unlatched position (indicated in phantom in FIGS. 3 and 4). The slide 28 is mounted to the body 18 by a screw 30 which extends through an elongated slot 32 provided in the slide 28.

One end 34 of the slot 32 cooperates with the screw 30 to define the latched position of the slide 28, the slide 28 being urged or biased into its latched position by a pair of springs 36 housed in a cavity 38 formed between the slide 28 and the body 18 of the handle 16. One end of each of the springs 36 is in constant engagement with an abutment 40 provided within the body 18 of the handle 16, while an opposite end of each of the springs 36 is in constant engagement with a shoulder 42 provided on the slide 28. In its latched position, the slide 28 extends through an opening 44 provided in a crossbar 46 of the frame 14, the slide 28 being arranged close enough to the crossbar 46 to inhibit movement of the handle 16 relative to the frame 14.

An opposite end 48 of the slot 32 cooperates with the screw 30 to define the unlatched position of the slide 28, which is provided with a trigger 50 so that the slide 28 can be engaged by a finger of a dentist or his or her assistant and then manually moved from its latched position to its unlatched position against the resisting force of the springs 36. In its unlatched position, the slide 28 permits relative movement between the handle 16 and the frame 14, thereby permitting the partial or complete removal of the handle 16 from the frame 14. When the trigger 50 is released, the springs 36 function to automatically move the slide 28 from its unlatched position to its latched position.

Referring still to FIGS. 2-4, the latching mechanism 22 includes a slide 52 which is slideably received within the body 18 adjacent to the handgrip 26 such that the slide 52 can be moved between a latched position (indicated by solid lines in FIGS. 3 and 4) and an unlatched position (indicated in phantom in FIGS. 3 and 4). The slide 52 is mounted to the body 18 by a screw 54 which extends through an elongated slot 56 provided in the slide 52.

One end 58 of the slot 56 cooperates with the screw 54 to define the latched position of the slide 52, the slide 52 being urged or biased into its latched position by a pair of springs 60 housed in a cavity 62 formed between the slide 52 and the body 18 of the handle 16. One end of each of the springs 60 is in constant engagement with an abutment 64 provided within the body 18 of the handle 16, while an opposite end of each of the springs 60 is in constant engagement with a shoulder 66 provided on the slide 52. In its latched position, the slide 52 extends through an opening 68 provided in the crossbar 46 of the frame 14, the slide 52 being arranged close enough to the crossbar 46 to inhibit movement of the handle 16 relative to the frame 14.

An opposite end 70 of the slot 56 cooperates with the screw 54 to define the unlatched position of the slide 52, which is provided with a trigger 72 so that the slide 52 can be engaged by a finger of a dentist or his or her assistant and then manually moved from its latched position to its unlatched position against the resisting force of the springs 60. In its unlatched position, the slide 52 permits relative movement between the handle 16 and the frame 14, thereby permitting the partial or complete removal of the handle 16 from the frame 14. When the trigger 72 is released, the springs 60 function to automatically move the slide 52 from its unlatched position to its latched position.

In use, the handle 16 facilitates the positioning of the dental light fixture through the provision of the handgrips 24, 26, both of which are arranged so as to be readily accessible to the dentist or his or her assistant. The handle 16 is preferably made of high-temperature plastic so that it can withstand sterilization temperatures while providing low thermal conductivity. Because the handgrips 24, 26 are formed integrally with the body 18 of the handle 16, it is advantageous to make the handle 16 out of a material having low thermal conductivity in order to inhibit excessive heating of the handgrips 24, 26. The location of the handle 16 in front of the shield 14 is also advantageous because it aids in the protection of the light bulb contained in the housing 10.

It will be understood that the embodiment described herein is merely exemplary and that a person skilled in the art may make many variations and modifications without departing from the spirit and scope of the invention. For example, the attaching means could constitute a wide variety of latch mechanisms, including different spring devices, and could operate from the handle or the frame, with such devices being located either on the handle or the frame. All such variations and modifications are intended to be included within the scope of the invention as defined in the appended claims.

We claim:

1. A unitary, quick-release handle for use on a dental, medical or similar lighting fixture, said handle comprising a first handgrip located at one end thereof, a second handgrip located at an opposite end thereof and attaching means located between said ends of said handle for releasably attaching said handle to a lighting fixture.

2. A handle according to claim 1, wherein said handle includes a body positioned between said first and second handgrips.

3. A handle according to claim 2, wherein said first and second handgrips are formed integrally with said body.

4. A handle according to claim 3, wherein said handle is molded from a high-temperature plastic, whereby said handle can withstand sterilization temperatures when it is removed from a lighting fixture while providing low thermal conductivity when it is attached to a lighting fixture.

5. A handle according to claim 2, wherein said attaching means includes first latching means positioned within said body adjacent to said first handgrip for releasably latching said handle to a lighting fixture frame on one side thereof and second latching means positioned within said body adjacent to said second handgrip for releasably latching said handle to the lighting fixture frame on an opposite side thereof.

6. A handle according to claim 5, wherein said first latching means includes a first slide and first mounting means for mounting said first slide to said body such that said first slide is movable between a first position in which said first slide is engageable with the lighting fixture frame and a second position in which said first slide is disengageable from the lighting fixture frame; and wherein said second latching means includes a second slide and second mounting means for mounting said second slide to said body such that said second slide is movable between a first position in which said second slide is engageable with the lighting fixture frame and a second position in which said second slide is disengageable from the lighting fixture frame.

7. A handle according to claim 6, wherein said first latching means includes first urging means for urging said first slide into its said first position; and wherein said second latching means includes second urging for urging said second slide into its said first position.

8. A handle according to claim 7, wherein said first urging means includes at least one spring; and wherein said second urging means includes at least one spring.

9. A handle according to claim 7, wherein said first latching means includes a first trigger sized and shaped so as to be engageable by a finger of an operator who can thereby manually move said first slide from its said first position to its said second position; and wherein said second latching means includes a second trigger sized and shaped so as to be engageable by a finger of an operator who can thereby manually move said second slide from its said first position to its said second position.

10. A lighting fixture for dental, medical or any similar use, comprising a housing; a frame surrounding said housing; a light source mounted in said housing; a shield extending across said housing in front of said light source; and a handle extending transversely across said housing from one side thereof to an opposite side thereof, said handle including a first handgrip located at one end thereof, a second handgrip located at an opposite end thereof, a body positioned between said first and second handgrips and bridging said shield and attaching means located between said ends of said handle for releasably attaching said handle to said frame.

11. A lighting fixture according to claim 10, wherein said first and second handgrips are formed integrally with said body.

12. A lighting fixture according to claim 11, wherein said handle is molded from a high-temperature plastic, whereby said handle can withstand sterilization temperatures when it is removed from said housing while providing low thermal conductivity when it is attached to said housing.

13. A lighting fixture according to claim 10, wherein said attaching means includes first latching means positioned within said body adjacent to said first handgrip for releasably latching said handle to said frame on one side of said housing and second latching means positioned within said body adjacent to said second handgrip for releasably latching said handle to said frame on an opposite side of said housing.

14. A lighting fixture according to claim 13, wherein said first latching means includes a first slide and first mounting means for mounting said first slide to said body such that said first slide is movable between a first position in which said first slide is engageable with said frame and a second position in which said first slide is disengageable from said frame; and wherein said second latching means includes a second slide and second mounting means for mounting said second slide to said body such that said second slide is movable between a first position in which said second slide is engageable with said frame and a second position in which said second slide is disengageable from said frame.

15. A lighting fixture according to claim 14, wherein said first latching means includes first urging means for urging said first slide into its said first position; and wherein said second latching means includes second urging for urging said second slide into its said first position.

16. A lighting fixture according to claim 15, wherein said first urging means includes at least one spring; and wherein said second urging means includes at least one spring.

17. A lighting fixture according to claim 15, wherein said first latching means includes a first trigger sized and shaped so as to be engageable by a finger of an operator who can thereby manually move said first slide from its said first position to its said second position; and wherein said second latching means includes a second trigger sized and shaped so as to be engageable by a finger of an operator who can thereby manually move said second slide from its said first position to its said second position.

18. A lighting fixture according to claim 17, wherein said first trigger extends outwardly from said first slide; and wherein said second trigger extends outwardly from said second slide.

* * * * *